(12) United States Patent
Nikiforov et al.

(10) Patent No.: US 8,053,541 B2
(45) Date of Patent: Nov. 8, 2011

(54) CATALYSTS FOR CATALYTIC CHAIN TRANSFER

(75) Inventors: Gregory A. Nikiforov, Moscow (RU); Alexei A. Gridnev, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 128 days.

(21) Appl. No.: 12/715,483

(22) Filed: Mar. 2, 2010

(65) Prior Publication Data

US 2010/0160582 A1    Jun. 24, 2010

Related U.S. Application Data

(62) Division of application No. 11/595,174, filed on Nov. 9, 2006, now Pat. No. 7,714,084.

(51) Int. Cl.
*C08F 118/02* (2006.01)
*B01J 31/18* (2006.01)

(52) U.S. Cl. ........ 526/319; 526/320; 526/346; 526/335; 502/167; 556/32; 556/35

(58) Field of Classification Search .................. 526/319, 526/320, 346, 335; 502/167; 556/32, 35
See application file for complete search history.

(56) References Cited

U.S. PATENT DOCUMENTS

| 5,726,263 A | * | 3/1998 | Gridnev | ........................ 526/147 |
| 5,750,772 A | | 5/1998 | Gridnev | |
| 6,858,745 B2 | * | 2/2005 | Gridnev et al. | ................. 556/35 |

OTHER PUBLICATIONS

Gridnev, A., and Ittel S.D.; Chem Rev. 101:3611-60 (2001); "Catalytic Chain Transfer in Free Radical Polymerization".

* cited by examiner

*Primary Examiner* — Ling Choi
(74) *Attorney, Agent, or Firm* — Gann G. Xu

(57) ABSTRACT

Cobaloxime derivatives and methods of producing cobaloxime derivatives are disclosed herein. Methods of producing decolorized homo- and co-polymers through polymerization of monomers in presence of the cobaloxime derivatives and decolorization of the produced polymer by exposing the polymer to a sorbent and, optionally, a solvent are also disclosed herein.

7 Claims, No Drawings

CATALYSTS FOR CATALYTIC CHAIN TRANSFER

CROSS-REFERENCE TO RELATED APPLICATION

This application is a divisional of U.S. application Ser. No. 11/595,174, filed on Nov. 9, 2006, now allowed, which claims priority under 35 U.S.C. §119 from U.S. Provisional Application Ser. No. 60/735,960, filed Nov. 10, 2005.

FIELD OF THE INVENTION

This invention relates to cobaloxime derivatives and a process for making said cobaloxime derivatives. This invention also relates to a process for making colorless oligomers using a catalytic chain transfer catalyst/sorbent combination.

BACKGROUND OF THE INVENTION

Making oligomers by catalytic chain transfer (CCT) is inexpensive and technologically convenient. One problem with CCT, however, is removal of the CCT catalyst from the final product. Since current CCT catalysts are based on cobalt chelates, the CCT catalysts are inherently colored. This color cannot be tolerated by some oligomers such as those designed for use in clearcoats.

One solution is to pass the reaction mixture through sorbents (see U.S. Pat. Nos. 5,726,263 and 5,750,772). This approach, however, requires addition of at least 50% more additional solvent. This solvent must be removed later. Thus, the dilution adds additional cost to the process.

There remains a need for making colorless oligomers through CCT in a convenient and inexpensive way.

SUMMARY OF THE INVENTION

This invention provides cobaloxime derivatives having the formula:

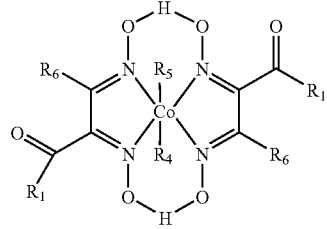

(I)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

Also provided herein are cobaloxime derivatives having the formula:

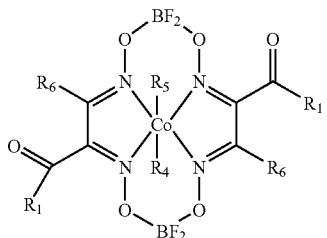

(II)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

Another aspect is for a method of producing a cobaloxime derivative comprising:
(a) contacting a cobalt salt with a dioxime in the presence of a solvent capable of dissolving the cobalt salt, optionally in the presence of a Lewis base compound, wherein the dioxime has the formula:

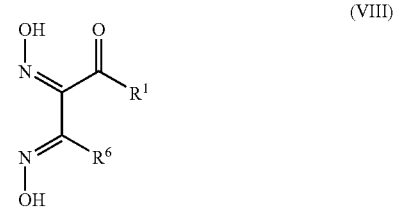

(VIII)

wherein $R^1$ is $OR^2$, $NHR^2$, or $NR^2R^3$; $R^2$ and $R^3$ are, independently, alkyl, substituted alkyl, aryl, substituted aryl, or hydrogen; and $R^6$ is alkyl or substituted alkyl; and
(b) optionally, recovering the cobaloxime derivative produced by the reaction of step (a).

This invention also provides a method of producing decolorized homo- and co-polymers comprising:
(a) polymerizing at least one monomer in the presence of a cobaloxime derivative; and
(b) decolorizing the polymer produced by step (a) by exposing the polymer to a sorbent and, optionally, a solvent.

Cobaloxime derivatives can be represented by the formula:

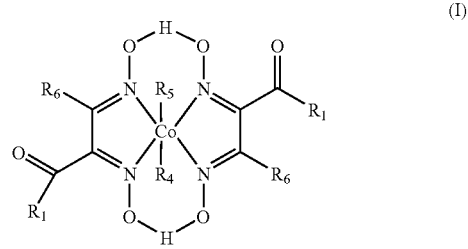

(I)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

Alternatively, cobaloxime derivatives can be represented by the formula:

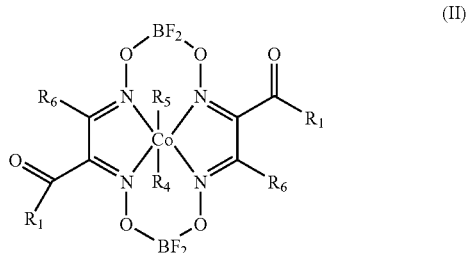

(II)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

Preferred cobaloxime derivatives include, for example,

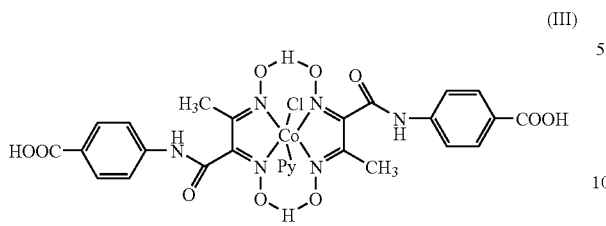
(III)

wherein Py is 4-(dimethylamino)pyridine;

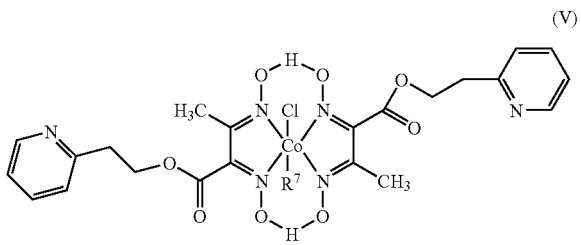
(V)

wherein $R^7$ is 4-(dimethylamino)pyridine;

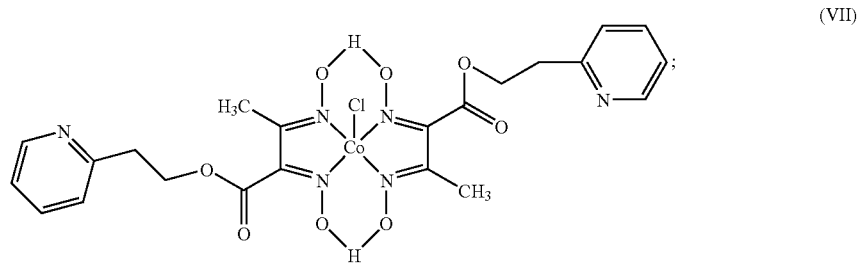
(VII)

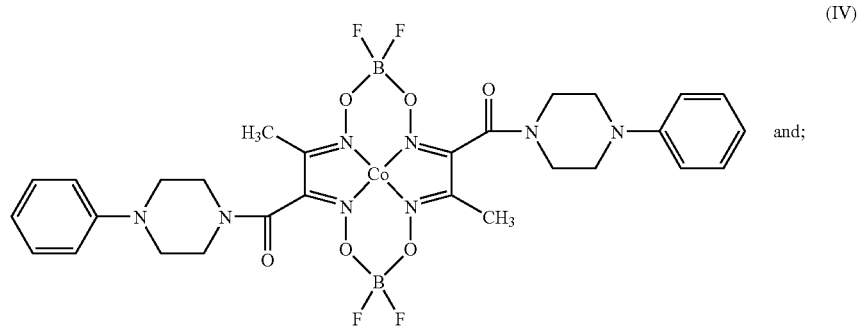
(IV)

and;

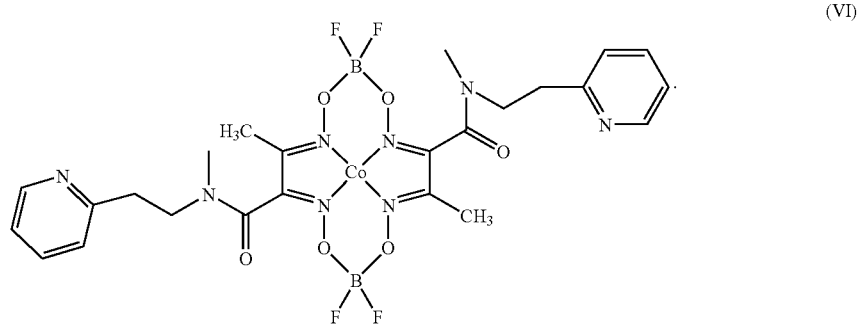
(VI)

Other objects and advantages of the present invention will become apparent to those skilled in the art upon reference to the detailed description that hereinafter follows.

DETAILED DESCRIPTION OF THE INVENTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Applicants have found that catalytic chain transfer (CCT) catalyst removal requires no solvent addition if monomer polymerization is effectuated by specially designed catalysts. The catalysts are cobaloxime derivatives, which can be separated from a polymerization mixture by addition of a sorbent. The resulting oligomeric mixture can be then filtered by any method as is known to one of ordinary skill in the art to remove the sorbent containing absorbed CCT catalyst to yield a substantially to completely colorless polymer solution.

Cobaloxime derivatives can be represented by the formula:

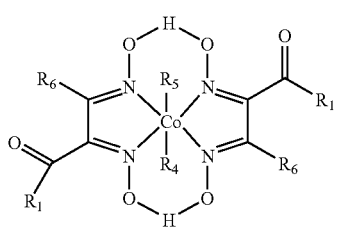

(I)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

In another embodiment, cobaloxime derivatives can be represented by the formula:

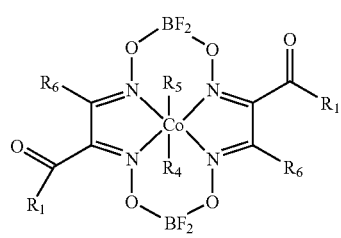

(II)

wherein $R^1$ is $OR^2$, $NHR^2$, or $NR^2R^3$; $R^2$ and $R^3$ are, independently, alkyl, substituted alkyl, aryl, substituted aryl, or hydrogen; $R^4$ is absent, alkyl, substituted alkyl, halogen, OH, or water; $R^5$ is absent or a Lewis base; and $R^6$ is alkyl or substituted alkyl.

In one aspect, the invention provides a process for producing cobaloxime derivatives disclosed herein. In a first step, a cobalt salt, preferably but not limited to acetate or chloride, and, optionally, a Lewis base compound are contacted with a dioxime in a solvent that dissolves the cobalt salt. Preferably, the solvent is an alcohol. Dioximes useful in the present invention have the formula

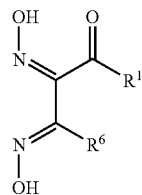

(VIII)

wherein $R^1$ is $OR^2$, $NHR^2$, or $NR^2R^3$; $R^2$ and $R^3$ are, independently, alkyl, substituted alkyl, aryl, substituted aryl, or hydrogen; and $R^6$ is alkyl or substituted alkyl.

Synthesis of glyoxime ligand is based on tert-butyl acetoacetate reaction with corresponding amine or alcohol. Simple heating of their mixture provides a desired substituted acetoacetate.

In an exemplary embodiment, synthesis of α-pyridilethyl ester of acetoacetic acid is as follows. A mixture of 16.3 ml (0.1 M) t-butylic ester of acetoacetic acid and 11.3 ml (0.1 M) 2-α-pyridilethanol was heated for 1 hour at 130-135° C. at atmospheric pressure removing t-butanol at the same time. The residue was distilled under vacuum.

The obtained ester or amide of acetoacetic ester then undergoes nitrosation. A typical nitrosation of an α-pyridilethyl ester of acetoacetic acid is a follows. Into a solution of 14.7 g (0.071 M) of ester in 100 ml acetic acid was added portionwise 5.4 g (0.078 M) of $NaNO_2$ with stirring at 10-12° C. The mixture was stirred for 2 hours at 20° C., then diluted with water to 400 ml. The crystals were separated, washed with water, and dried under vacuum. 11.9 g of monoxime has been obtained.

Obtained mono-nitroso acetoacetate reacts further with hydroxylamine by typical procedure as is known to one of ordinary skill in the art.

Based on these teachings, one of ordinary skill in the art can make the necessary adjustments to synthesize any of the cobaloxime derivatives described herein.

Optionally, the cobaloxime forming reaction can be effectuated in the presence of a Lewis base compound. Preferred Lewis base compounds are pyridines, phosphines, imidazoles, and water. More preferred are pyridines and imidazoles. Most preferred is 4-dimethylaminopyridine.

In a second, optional step, the cobaloxime derivative can be recovered from the reaction mixture by any method as known to one of ordinary skill in the art (e.g., by separation and washing with water and MeOH (5 ml) and drying in vacuum over $P_2O_5$).

Conversion of H-bridged cobaloximes described herein to boron derivative-bridged cobaloximes described herein can be effectuated by any method as is known in the art. For example, to a suspension of a synthesized H-bridged cobaloxime described herein in ethyl ether in argon flow, pyridine is added. The mixture is then cooled to 4° C., and a boron derivative, preferably a boron trialcoxide or a boron trihalogenate, and more preferably $BF_3.Et_2O$, is added with active stirring. The mixture is stirred for about 10 hr at 20° C. The boron derivative-bridged cobaloxime precipitate is separated, washed with water, and dried under vacuum over $P_2O_5$ to constant weight.

Another aspect of the invention is a method of producing decolorized homo- and co-polymers comprising:
(a) polymerizing at least one monomer in the presence of a cobaloxime derivative; and
(b) decolorizing the polymer produced by step (a) by exposing the polymer to a sorbent and, optionally, a solvent.

Polymerization of monomers in the presence of cobaloximes as catalytic chain transfers is well known. See, e.g., Gridnev, A., and Ittel, S. D., "Catalytic Chain Transfer in Free Radical Polymerization." Chem. Rev. 101:3611-60 (2001) and references therein.

By "polymerizing at least one monomer" is meant that a single monomer can be polymerized to form a homopolymer or two or more different monomers can be polymerized to form a co-polymer. Methacrylates are preferred monomers, but other monomers can be used as well, including, but not limited to, acrylates, styrene, alpha-methylstyrene and other substituted styrenes, maleates, itaconates, alpha-methylbutylroacetone, and chloropene. Monomers can be polymerized in bulk or in a solvent. Typically, 10-2000 ppm of cobaloxime is added, and polymerization proceeds in regular way as is known to one of ordinary skill in the art of radical polymerization.

Preferred methacrylate monomers include butyl methacrylate, 2-hydroxyethyl methacrylate, and glycidylmethacrylate.

In the decolorization step, any polymer sorbent with ionizable groups can be used to remove the cobaloxime derivative from the reaction mixture. Non-limiting examples of useful sorbents include basic alumina, a basic exchange resin, an acidic exchange resin, and activated carbon. Preferably, the sorbent is basic alumina. Sorbents are added to the reaction mixture after the reaction is finished. After stirring for about 10 minutes to about 12 hours, preferably about 20 minutes to about four hours, the sorbents are filtered off. Optionally, sorbents can be used to filter reaction mixture through. Typically, sorbents are used at content of about 2 to about 40 weight percent of the reaction mixture. The exact amount of sorbent depends on the concentration of the cobaloxime in the reaction mixture. The greater the amount of cobaloxime used, the more sorbent is required to remove the catalyst from the reaction mixture.

Optionally, solvents can be used to aid in the removal of the cobaloxime derivative from the reaction mixture, especially when the molecular weight of the polymer is high. The higher the MW of the polymer, the more solvent is required to maintain low viscosity during the decolorization process. Higher viscosities in the reaction mixture lead to longer decolorization processes. Exemplary solvents include methyl ethyl ketone, isopropanol, methanol, ethylacrylate, butylacetate, toluene, xylene, and acetone. Preferred solvents are methyl ethyl ketone and isopropanol at a content of 80% or less.

Decolorized homopolymers and co-polymers produced as described herein are particularly useful in clearcoat coating compositions. Decolorized homopolymers and co-polymers can also be used, for example, in dental applications and in making hydrogels for contact lenses and other optical applications.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modifications of the invention to adapt it to various uses and conditions.

The meaning of abbreviations is as follows: "CCT" means catalytic chain transfer, "HEMA" means 2-hydroxyethyl methacrylate, "GPC" means gel permeation chromatography, "MMA" means methyl methacrylate, "BMA" means butyl methacrylate, "GMA" means glycidyl methacrylate, "PDI" means polydispersity index, and "APHA" means American Public Health Association.

General Polymerization Procedure

All ingredients, including solvent, are mixed in air and placed into a reactor equipped with stirrer and a reflux condenser. The mixture is deoxigenized by passing nitrogen through it for 25 minutes. Temperature is raised to required limits and polymerization proceeds upon adequate stirring at indicated amount of time.

Obtained polymer solution is chilled down to room temperatures and dispensed into airtight containers. Molecular weights are obtained using gel-permission chromatography in tetrahydrofuran as a solvent at 30° C. with help of chromatography columns packed with styrogels.

Color of the polymerization products was determined using APHA standard solutions by visual comparison.

Example 1

Synthesis of Catalyst III 2.7 g (0.01M) of dioxime and 0.62 g (0.005 M) 4-dimethylaminopyridine were added into solution of 1.19 (0.005 M) $CoCl_2.6H_2O$ in 50 ml MeOH. The mixture was stirred in airflow for 3 hr at 20° C. When the mixture became clear and little yellow crystals appeared, 50 ml of water were added. The crystals were separated and washed with water and MeOH (5 ml) and dried in vacuum over $P_2O_5$.

Example 2

Synthesis of Catalyst IV

A mixture of 16.5 ml (0.1 M) of tert-butylacetylacetate and 12.7 ml (0.1 M) of N-phenylpiperazine was heated at 130-140° C. for 1 hr with removal of tert-butanol from the reaction zone in argon flow. The residue was cooled, dissolved in 100 ml of methanol, cooled to 4-6° C., and 7 ml (0.1 M) of acetyl chloride was added drop-wise so that the temperature did not exceed 6° C. Methanol was removed under vacuum, the residue was heated with 150 ml of benzene, and the solution was decanted. The resin was treated with 100 ml of acetone. The crystals of N-phenyl-piperazine hydrochloride were separated. The mother solution was evaporated under vacuum to ~40 ml and cooled to −10° C. (in freezer). The crystals of amide hydrochloride were separated and rinsed with acetone and hexane. Applicants obtained 17.5 g of white crystals (melting point 131-132° C.) with a yield of 73%.

To a suspension of 4 g (0.005M) of the H-bridged cobaloxime in 50 ml ethyl ether in argon flow, 1.6 ml (0.02 M) of pyridine was added. The mixture was cooled to 4° C. and 3.8 ml (0.03 M) of $BF_3.Et_2O$ was added during 30 min with active stirring. The mixture was stirred for 10 hr at 20° C. The precipitate was separated, washed with water, dried under vacuum over $P_2O_5$ to constant weight.

Example 3

Synthesis of Catalyst V

The solution of 1.07 g (0.0045 M) $CoCl_2.H_2O$ in 25 ml of MeOH was added into solution with 2.29 g (0.009 M) dioxime and 1.1 g (0.009 M) 4-dimethylaminopyridine in 40 ml MeOH with stirring at 20° C. Intensively red solution was stirred for 2 hr in airflow. Cobaloxime was precipitated with the slow addition (≈ for 3 h) of 250 ml of water with strong stirring at 4-6° C. The product was separated, washed with water, and transprecipitated from 25 ml MeOH with 100 ml of water at the same conditions. 2.5 g of dark brown powder of cobaloxime was obtained, with a yield of 78%.

Example 4

Synthesis of Catalyst VI

To a solution of 3.1 g (0.012 M) of dioxime and 1.43 g (0.006 M) $CoCl_2.6H_2O$ at 4° C. in argon flow, 0.97 ml (0.012 M) of pyridine and, during 30 min, a solution of 0.53 g (0.013 M) of NaOH in 15 ml of methanol were added. The mixture was stirred for 1 hr at 20° C. The obtained dark red-colored solution was evaporated under vacuum at 30-35° C.; a residue was dried by azeotropic distillation under vacuum with 50 ml benzene at 30-35° C. The residue was treated with 75 ml of acetone; resinous crystals were separated and rinsed with acetone. After acetone evaporating at 30° C., dark red resin was dried under vacuum over $P_2O_5$ to constant weight.

To a suspension of 4 g (0.005M) of the H-bridged cobaloxime in 50 ml ethyl ether in argon flow, 1.6 ml (0.02 M) of pyridine was added. The mixture was cooled to 4° C. and 3.8 ml (0.03 M) of $BF_3.Et_2O$ was added during 30 min with active stirring. The mixture was stirred for 10 hr at 20° C. The precipitate was separated, washed with water, dried under vacuum over $P_2O_5$ to constant weight.

Example 5

Synthesis of Catalyst VII

The solution of 2.38 g (0.01 M) $CoCl_2.6H_2O$ in 25 ml of MeOH was added quickly into a solution of 4.6 g (0.02M) of dioxime in 30 ml MeOH with stirring at 20° C. Red-brown solution was stirred intensively for 2 hr in air flower. Crystals were separated, washed with MeOH and acetone, and dried. Applicants obtained 2.6 g of yellow powder of cobaloxime, with a yield of 44%.

Example 6

Decolorization of a Product Obtained with Catalyst III

Polymerization solution consisting of 35 ml HEMA, 35 ml isopropanol, 0.6 g VAZO® 67 (substituted azonitrile compound, available from E.I. du Pont de Nemours & Co., Wilmington, Del.), and 50 mg of catalyst III (see Example 1) in 4 ml of pirrolidininone was kept 3 hours at 85° C. Catalyst III has the formula:

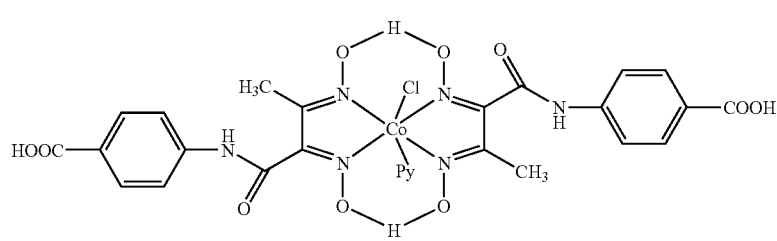

(III)

wherein Py is 4-(dimethylamino)pyridine.

GPC analysis indicated formation of polyHEMA having an Mn=880 and a PDI=1.81. Color of the reaction mixture was determined to be APHA=1200. Decolorization was conducted by stirring with a basic ion-exchange resin, Amberlite® IRA-900 (strong base (quaternary ammonium chloride) ion exchange resin, available from Rohm & Haas, Philadelphia, Pa.), at 90° C. for 90 minutes. About 3 g of Amberlite® IRA-900 was taken to decolorize 70 ml of the polyHEMA solution down to APHA=150.

Example 7

Comparison Experiment with Example 6

The polymerization was conducted the same way as described in the Example 6, but catalyst VIII was used instead of catalyst III. Catalyst VIII has the formula:

(VIII)

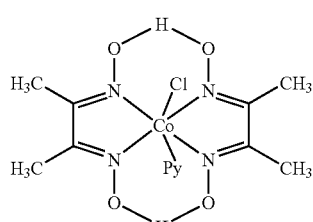

wherein Py is pyridine.

Decolorization was conducted the same way reduced color from 1500 to APHA=900, which was substantially less decolorization than in Example 6.

Example 8

Decolorization of a Product Obtained with Catalyst III (Different Monomer)

Polymerization solution consisting of 35 ml MMA, 15 ml dichloroethane, 50 mg HEMA, 0.6 g of VAZO® 67, and 30 mg of catalyst III in 2 ml of pirrolidininone was kept 3 hours at 85° C. (see Example 6 infra for the formula of catalyst III). A polymer solution was obtained having an Mn=1840 and a DPI=2.02. Decolorization was conducted by adding 20 ml methanol to reduce viscosity and 3 g of Amberlite® IRA-900. After 2 hours of stirring at 70° C., color was reduced from APHA=1500 to 200.

Example 9

Decolorization of a Product Obtained with Catalyst IV

Polymerization solution consisting of 25 ml HEMA, 25 ml isopropanol, 0.25 g of VAZO® 67, and 15 mg of catalyst IV (see Example 2) in 4 ml of acetone was kept 4 hours at 85° C. Catalyst IV has the formula:

(IV)

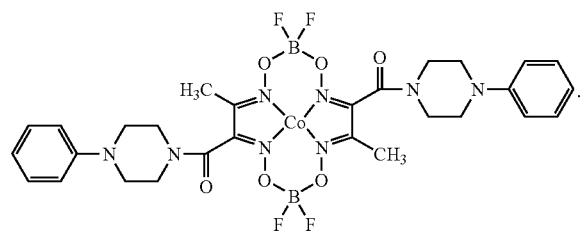

GPC analysis indicated formation of polyHEMA having an Mn=1810 and a DPI=2.53. Color of the reaction mixture was determined to be APHA=2100. Decolorization was conducted by passing the reaction mixture through silicagel (15% of reaction volume). Final color index of the solution was APHA=350.

Example 10

Comparison Experiment with Example 9

The polymerization was conducted the same way as described in Example 9, but catalyst IX was used instead of catalyst IV. Catalyst IX has the formula:

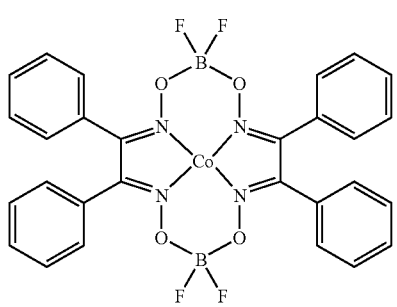

Decolorization conducted the same as in Example 9 did not change the APHA of the polymer.

Example 11

Decolorization of a Product Obtained with Catalyst V (Different Monomer)

Polymerization solution consisting of 25 ml BMA, 25 ml methanol, 0.25 g of VAZO® 67, and 50 mg of catalyst V (see Example 3) in 4 ml of acetone was kept 4 hours at 85° C. Catalyst V has the formula:

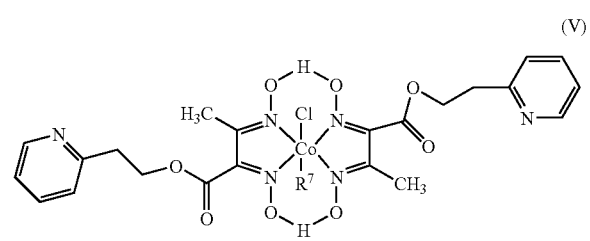

wherein $R^7$ is 4-(dimethylamino)pyridine.

Polymerization mixture with color index APHA=2200 was stirred with 2 g Amberlyst™ 15 (strongly acidic, sulfonic acid, macroreticular polymeric resin based on crosslinked styrene divinylbenzene copolymers, available from Rohm & Haas, Philadelphia, Pa.) for 60 minutes. After the treatment, APHA was determined to be 250.

Example 12

Decolorization of a Product Obtained with Catalyst VI (Different Monomer)

Polymerization solution consisting of 15 ml MMA, 10 ml GMA, 25 ml butylacetate, 0.25 g of VAZO® 67, and 60 mg of catalyst VI (see Example 4) in 4 ml of acetone was kept 4 hours at 85° C. Catalyst VI has the formula:

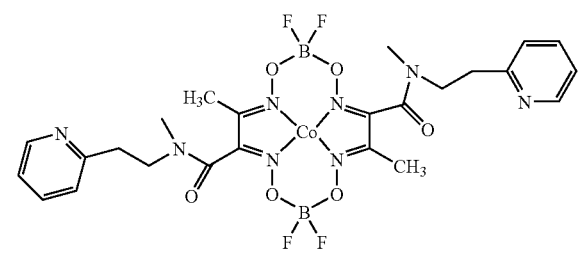

Polymerization mixture with color index APHA=2700 was stirred with 2 g DOWEX® 50WX2-200 (strong acid cation exchange resin based on a microporous copolymer of styrene and divinylbenzene, available from Dow Chemical Co., Midland, Mich.) for 60 minutes. After the treatment, APHA was determined to be 300.

Example 13

Decolorization of a Product Obtained with Catalyst II (a Comparison with Example 12)

Polymerization was conducted similar to that described in Example 12 but with catalyst IX instead of catalyst VI (see Example 10 infra for the formula of catalyst IX). Decolorization with DOWEX® 50WX2-200 ion-exchange resin reduced APHA from 2000 to 1800, which was substantially less decolorization than in Example 12.

We claim:
1. A cobaloxime derivative having the formula:

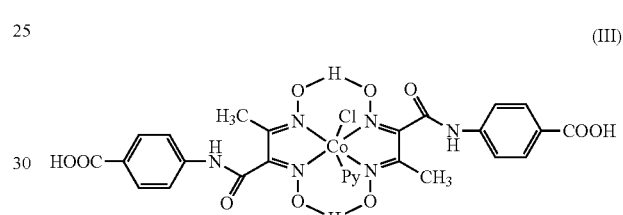

wherein Py is 4-(dimethylamino)pyridine, or

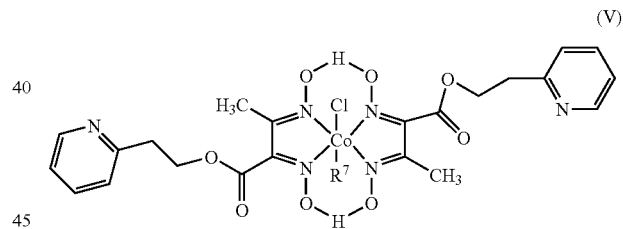

wherein $R^7$ is 4-(dimethylamino)pyridine, or

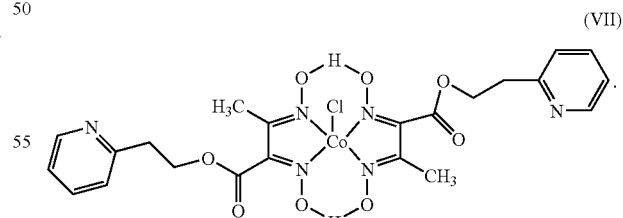

2. A method of producing decolorized homo- and co-polymers comprising:
(a) polymerizing at least one monomer in the presence of a cobaloxime derivative; and
(b) decolorizing the polymer produced by step (a) by exposing the polymer to a sorbent and, optionally, a solvent;

wherein the cobaloxime derivative has the formula

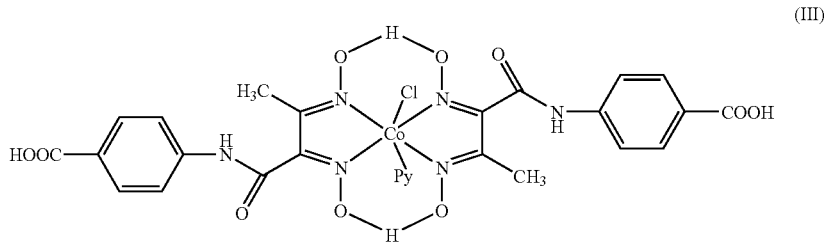

(III)

wherein Py is 4-(dimethylamino)pyridine, or

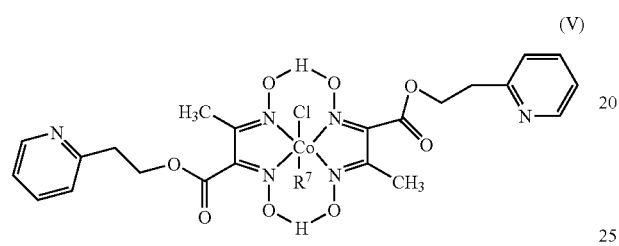

(V)

wherein $R^7$ is 4-(dimethylamino)pyridine, or

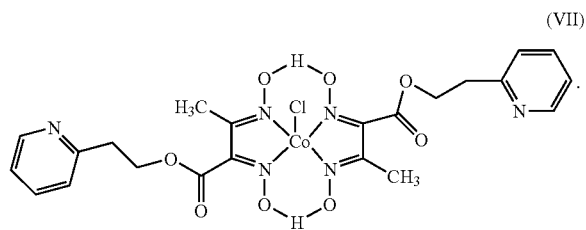

(VII)

3. The method of claim 2, wherein the at least one monomer is a methacrylate monomer, an acrylate monomer, a styrene monomer, a substituted styrene monomer, a maleate monomer, an itaconate monomer, an alpha-methylbutylroacetone monomer, or a chloropene monomer.

4. The method of claim 3, wherein the methacrylate monomer is butyl methacrylate, 2-hydroxyethyl methacrylate, or glycidylmethacrylate.

5. The method of claim 2, wherein the sorbent is basic alumina, a basic exchange resin, an acidic exchange resin, or activated carbon.

6. The method of claim 2, wherein the solvent is methyl ethyl ketone, isopropanol, methanol, ethylacetate, butylacetate, toluene, xylene, or acetone.

7. The method of claim 2, wherein the decolorized polymer of step (b) has an APHA of less than about 400.

* * * * *